United States Patent [19]

Schade et al.

[11] 4,452,954

[45] Jun. 5, 1984

[54] POLYESTER VARNISHES

[75] Inventors: Gerhard Schade; Martin Schmitthenner, both of Witten; Norbert Volkommer, Troisdorf-Kriegsdorf, all of Fed. Rep. of Germany

[73] Assignee: Dynamit Nobel AG, Cologne, Fed. Rep. of Germany

[21] Appl. No.: 412,431

[22] Filed: Aug. 27, 1982

[30] Foreign Application Priority Data

Sep. 2, 1981 [DE] Fed. Rep. of Germany ....... 3134640

[51] Int. Cl.$^3$ ............................................. C08L 67/02
[52] U.S. Cl. .................................. 525/440; 525/441; 528/298; 524/539; 427/388.2; 427/388.3
[58] Field of Search ................. 525/440, 441; 528/298

[56] References Cited

U.S. PATENT DOCUMENTS

| | | | |
|---|---|---|---|
| 3,822,240 | 7/1974 | Schmitt | 525/440 |
| 4,129,681 | 12/1978 | Anderson | 525/441 |
| 4,151,152 | 4/1979 | Schmitt | 525/440 |
| 4,169,825 | 10/1979 | Yapp | 525/440 |
| 4,186,227 | 1/1980 | Wulff | 525/441 |
| 4,190,714 | 2/1980 | Isaken | 525/441 |
| 4,217,377 | 8/1980 | Shay | 525/441 |
| 4,246,380 | 1/1981 | Gras | 525/440 |
| 4,247,666 | 1/1981 | Mochizuki | 525/440 |
| 4,261,873 | 4/1981 | Laganis | 525/441 |
| 4,284,745 | 8/1981 | Meyer | 525/440 |

FOREIGN PATENT DOCUMENTS 2934443  3/1981  Fed. Rep. of Germany .

Primary Examiner—John C. Bleutge
Assistant Examiner—Patricia Short
Attorney, Agent, or Firm—Felfe & Lynch

[57] ABSTRACT

Thermosetting coating substances containing as binding agent 5 to 35 weight-percent of triazine resins, especially benzoguanamine resins, or blocked polyisocyanate resins, and 95 to 65 weight-parts of saturated polyesters of terephthalic and/or isophthalic acids and 100 to 70 mole-% of bis-(hydroxymethyl)-tricyclodecane and 0 to 30 mole-% of additional diols, especially 2,2-dimethylpropanediol-1,3, yield varnish coatings on metals, which coatings are stable under sterilization conditions against acid contents in containers, especially acid foodstuff preparations.

10 Claims, No Drawings

POLYESTER VARNISHES

This invention relates to polyester varnishes, particularly varnishes capable of withstanding acid sterilization.

German Auslegeschrift No. 1,807,776 describes boiling water-resistant, sterilizable varnish films of amorphous copolyesters, which are very capable of withstanding forming stresses and are made substantially of tere- and isophthalic acid as well as alkylene glycols and 2,2-dimethylpropanediol-1,3, 5 to 30% of a benzoguanamine resin, 0.5 to 2% of acid catalysts, and pigments if desired. Such varnish films have a high surface hardness and at the same time good formability. Deep-drawn packing containers of thin sheet metal, pre-coated with such varnish films, are sterilizable in water at 121° C. without such damage to the varnish as loss of adhesion at dents or the absorption of moisture.

German Auslegeschrift No. 2,126,048 described varnish films which have substantially the same chemical composition as those of Auslegeschrift No. 1,807,776, but low glass transformation points between 30° and 50° C. and relative viscosities of 1.5 to 1.8 and still greater formability.

German Auslegeschrift No. 2,521,792 describes coating substances which contain aminoplastics and polyesters prepared from tere- or isophthalic acid and 5 to 50 mole-% of hexahydroterephthalic acid on the one hand, and on the other hand aliphatic diols and 2,2-dimethylpropanediol-1,3. Films of these coating substances have sufficiently good formability but under sterilization conditions in contact with acids they they have too little stability.

German Auslegeschrift No. 2,521,791 describes coating substances which contain aminoplastics and polyesters prepared from tere- or isophthalic acid on the one hand, and on the other hand aliphatic diols, 2,2-dimethylpropanediol-1,3 and 1,4-bis-hydroxymethylcyclohexane. These coating substances yield varnish films of sufficiently good formability, but they do not have sufficient stability under sterilization conditions in contact with acids.

German Offlenlegungsschrift No. 2,934,443 describes coating substances which contain aminoplastics and polyesters prepared from aromatic and, if desired, aliphatic and cycloaliphatic discarboxylic acids on the one hand, and on the other hand aliphatic diols, cycloaliphatic diols and 2,2-dimethylpropanediol-1,3 as well as 5 to 50 mole-percent of the diol component bis-(hydroxymethyl)-tricyclo -(5.2. 1.0$^{2,6}$) decane. These coating substances have adequate formability, but poor stability under sterilization conditions in contact with acids.

Under sterilization conditions in contact with acids, coating substances in accordance with this state of the art have little or no stability, so that their use as varnish is limited and they cannot be used as internal protective varnish for containers of sterilized acid foodstuffs. It has been possible by varying the diols and dicarboxylic acids to make polyesters into varnish resins which have proven to be sufficiently formable as varnish on sheet metal in the production of canned goods, for example, and to be resistant to boiling water in the sterilization of neutral contents, but there has been no indication that varnishes on the basis of polyesters could be resistant to the acid content of acid foodstuffs without damage or lifting of the varnish from the sheet metal. It has therefore been impossible to provide coatings on a basis of polyesters on containers for acid foodstuffs, such as vinegar preserves, fruit juices and concentrates, sauerkraut, canned fish with a vinegar content etc.

The problem existed of producing highly formable varnish films on the basis of linear, saturated polyesters of high molecular weight, which would have sufficient stability and adhesion to the base material of the container under sterilization conditions in contact with acids.

THE INVENTION

Surprisingly it has been found that this problem can be solved in accordance with the invention with coating substances on the basis of saturated, linear polyesters whose diol content amounts to from 100 mole-% to 70 mole-% of bis-hydroxymethyl)-tricyclodecane and whose dicarboxylic acid content consists of terephthalic acid and/or isophthalic acid and, if desired, up to 10 mole-% of additional dicarboxylic acids. The stability against the acid content of the fillings is excellent under sterilization conditions, in contrast to the low stability of coatings on the basis of the chemically closely related polyesters known for this purpose.

The subject matter of the invention is therefore thermosetting coating substances consisting of binding agents, solvents and, if desired, common varnish additives such as pigments, fillers and adjuvants, the binding agents consisting of:

(a) 5 to 35 weight-parts of triazine resins, preferably benzoguanamine resins, or capped polyisocyanate resins and (b) 95 to 65 weight-parts of saturated linear polyesters with relative viscosities between 1.3 and 1.8, having a dicarboxylic acid content consisting of moieties of terephthalic and/or isophthalic acid, as well as up to 10 mole-%, if desired, of moieties of additional dicarboxylic acids, and a diol content consisting of bis-(hydroxymethyl)-tricyclodecane and other diols, these coatings being characterized by the fact that the diol content consists of 100 to 70 mole-% of bis-(hydroxymethyl)-tricyclodecane and 0 to 30 mole-% of other diols.

Bis-(hydroxymethyl)-tricyclodecane is known in itself as a component of linear polyesters from German Offenlegungsschrift No. 1,495,667, but there is no reference therein to the superior properties of coating substances when its content in the polyester reaches or exceeds 70 mole-% of the diol content. Bis-(hydroxymethyl)-tricyclodecane, referred to hereinafter for brevity as TCD-diol, is a mixture of numerous isomers in which two hydroxymethyl groups can be in various positions on the rings and the rings can have spatial configurations different from one another.

The proportion of 0 to 30 mole-% of the diol component can consist of any desired aliphatic or cycloaliphatic diols. Preferably, the proportion consists entirely or mainly of 2,2-dimethylpropanediol-1,3. Smaller proportions of up to about 4 weight-% by additionally condensed other diols occur and do not interfere. Terephthalic acid is preferred as the dicarboxylic acid. Furthermore preferred are contents up to 50 mole-% of isophthalic acid plus terephthalic acid. Contents of other aromatic, aliphatic or cycloaliphatic are possible, but not preferred.

The polyesters used in accordance with the invention are prepared by known methods, preferably using condensation catalysts. Such methods are described, for example, in W. R. Sorenson, T. W. Campbell, Preparative Methods of Polymer Chemistry, Interscience Publishers, Inc., New York 1961, pp. 111 to 127, 298 to 304.

The polyesters used in accordance with the invention have a relative viscosity of 1.3 to 1.8, the ratio $\eta_{rel}=t_1/t_0$ being the relative viscosity, in which $t_1$ is the flow-through time of a solution of 1 g of polymer in 100 ml of a mixture of 60 weight-parts of phenol and 40 weight-parts of 1,1,2,2-tetrachloroethane, and $t_0$ is the flow-through time of the solvent mixture in a capillary viscosimeter at 25° C.

The polyesters have setting points of at least 90 to 95 to as much as about 130° C. The polyesters of Examples 1, 2 and 3 had setting points in the temperature ranges of 123° to 130° C., 114° to 121° C. and 111° to 117° C., respectively. The polyester of Example 4 displayed a still satisfactory setting point in the range around 98° C. The high setting points of the polyesters lead one to expect poor forming qualitites in the coating substances formulated therefrom. The finding of good forming qualtities in the coatings (cf. the impact forming quality according to the table) is therefore surprising.

The hydroxyl number of the polyesters is low, with values less than 5 in the upper relative viscosity range and values of no more than about 20 in the lower viscosity range.

The polyesters are surprisingly easily soluble in various common varnish solvents, such as for example mixtures of aromatic hydrocarbons in the boiling ranges of 150° and 200° C., respectively. Especially surprising is the very good solubility of polyesters having terephthalic acid as the sole acid component, and also the high solubility when they contain TCD-diol only or in a very high percentage, which cannot be further improved by a partial content of 2,2-dimethylpropanediol-1,3. The good solubility is thus in contrast to the low solubility of corresponding polyesters on the basis of conventional diols, especially also on the basis of 1,4-hydrocymethylcyclohexane.

Benzoguanamine resins are preferably used as triazine resins, but melamine resins, mixed in some cases with triazine or benzoguanamine resins can also be used. Preferably 25 to 35 weight-parts of benzoguanamine resins are used, and preferably 15 to 25 weight parts in the case of the triazine resins. Capped polyisocyanate resins are used preferably with polyesters in accordance with (b) in which the molar ratio of the -NCO-groups of the polyisocyanates to the hydroxyl groups of the polyesters is 0.8 to 1.25:1. Capped polyisocyanates are those which are prevented from reacting prematurely with hydroxyl groups of the polyesters at standard temperature by means of appropriate blocking agents, such as oximes or caprolactam, and do not split up and become reactive until exposed to the thermosetting temperatures.

For the preparation of the coating substances of the invention, effective hardening catalysts are added preferably to the starting varnish solutions. For triazine resins, these catalysts are especially sulfuric acid, phosphoric acid, hydrochloric acid, oxalic acid, benzenesulfonic acid and homologous alkylated benzenesulfonic acids such as, for example, dodecylbenzenesulfonic acid or the like, and their salts with bases which are volatile at higher temperatures, such as ammnonia, mono- di- and trialkylamines, morpholine, 2-amino-2-methyl-propanol-1 etc. For capped polyisocyanate resins, organic tin compounds, especially dibutyl tin dilaurate, are particularly usable as hardening catalysts, as are other catalysts commonly used for the formation of polyurethane.

Examples of fillers and/or pigments are titanium dioxide, chalk, silica, magnesium oxide and pigments in conventional amounts. Varnish adjuvants, such as for example wetting agents, antifoaming agents, thixotropic agents, etc., can also be used.

The coating substances of the invention are applied by known methods, preferably by rolling or spraying.

The invention is not limited to the coating of metel substrates with the thermosetting substances of the invention but extends also to other heat-resistant base materials, such as ceramic or vitreous substances. Even heat-resistant plastics, especially thermosets, can be coated with the substances of the invention.

The coating substances prepared in accordance with the above information have excellent properties for use as internal varnishes—so-called gold varnishes and white varnishes—for coating the interior of containers, especially as regards resistance to sterilization in contact with acids, plus good impact-forming qualities, surface hardness, and strength of adherence especially to metal substrates and print adhesion.

EXAMPLES

In the examples given below, the following test methods were used in determining the characteristics of known coating substances and those of the invention:

1. Sterilization Stability

A can for foodstuffs is stamped from a varnished blank (e.g., tinplate, 0.25 mm, E 1, passivation 311, or aluminum, 0.25 mm, anodized). The deep-drawn can is tested for sterilization stability (Test method of the Institut für Lebensmitteltechnologie und Verpackung der TU München, Specification 11, "Prüfverfahren für Konservendosenlacke" ]methods for testing can varnishes] Part 7: Verpackungs-Rundschau 30 (1979) No. 5, p. 38), but at 121° C. and 1 bar gauge pressure for 60 minutes, using the testing media named in the Table. In the Table, c and d are hardness tests with acids of elevated concentration which permit a more definite differentiation of the stability of the varnish. In the evaluation scale, 0 represents perfect, no etching or dulling; 1 represents slight dulling; 2, usable, slight etching; 3, unusable, etching or local loss of adhesion of the varnish to the can; 4 to 5 increasing etching or increasing loss of adhesion; 6 to 10, can metal increasingly corroded, severe to very severe etching or loss of adhesion.

2. Forming Qualities a Impact forming

Wedge-bend test (test method of the Institut für Lebensmitteltechnologie und Verpackung der TU München, Specification 11, "Prüfverfahren für Konservendosenlacke" [methods for testing can varnishes for foodstuffs], Part 5: Verpackungs-Rundschau 25 (1974) No. 6, technological-scientific supplement, pp 47–48); 0 mm best rating, 100 mm poorest.

b Erichsen cupping

Constriction of a groove (mm) in the circumference of the deep-drawn cup until cracking begins on the crest of the groove.

For purposes of comparison, Examples 1 to 5 and the prior-art examples A to C have comparable formulas and the same method of application. These examples will further explain the breadth of the invention.

EXAMPLE 1

18.8 parts by weight of a polyester which had been made from terephthalic acid and TCD-diol and an amount of ethylene glycol as an impurity of which most is removed afterward, and has a relative viscosity of 1.70, are dissolved in 43.9 weight-parts of a mixture of SOLVESSO 150 ® and SOLVESSO 200 ® in a ratio of 4:1 by weight, and pigmented with 23.3 weight-parts of titanium dioxide (rutile type). This pigment paste is ground in a pearl mill. Then it is made into a varnish with 12.3 weight-parts of a commercial benzoguanamine resin (MAPRENAL MF 980, delivered as a 62% solution in n-butanol) and 0.3 weight-parts of dodecylbenzenesulfonic acid as acid catalyst (CATALYST 600). The prepared varnish is spread with a spiral brayer onto a blank of tinplate 0.25 mm, E 1, passivation 311, and baked on for 15 minutes at 210° C. (thickness of dry coating approximately 10 μm).

EXAMPLE 2

The varnish preparation and application of Example 1 is repeated, the polyester having the same composition, but a relative viscosity of 1.53.

EXAMPLE 3

The varnish preparation and application of Example 1 is repeated, the polyester having the same composition, but a relative viscosity of 1.34.

EXAMPLE 4

The varnish preparation and application of Example 1 is repeated, the polyester consisting on the one hand, however, of terephthalic acid, and on the other hand of a diol mixture of TCD-diol and 2,2-dimethylpropanediol (1,3) in a molar ratio of 4:1, and having a relative viscosity of 1.63.

EXAMPLE 5

The varnish preparation and application of Example 1 is repeated, the polyester consisting on the one hand of a dicarboxylic acid mixture of terephthalic acid and isophthalic acid in a molar ratio of 1:1, and on the other hand of TCD-diol, and having a relative viscosity of 1.50.

EXAMPLE A (An example of the prior art)

Example 1 is repeated with the varnish formula given in Example 1, but with a polyester prepared from a dicarboxylic acid mixture consisting of terephthalic acid and isophthalic acid in a molar ratio of 1:1 and a diol mixture consisting of 2,2-dimethylpropanediol-1,3 and ethylene glycol in a molar ratio of 1:1 and a relative viscosity of 1.65 (corresponding to German Auslegeschrift No. 1,807,776).

EXAMPLE B (An example of the prior art)

Example 1 is repeated with the varnish formula given in Example 1, but with a polyester prepared from a dicarboxylic acid mixture consisting of terephthalic acid and isophthalic acid in a molar ratio of 9:11 and a diol mixture consisting of 1,4-hydroxymethylcyclohexane, 2,2-dimethylpropanediol-1,3 and ethylene glycol in a molar ratio of 25:70:5 and a relative viscosity of 1.68 (corresponding to German Auslegeschrift No. 2,521,791).

EXAMPLE C (An example of the prior art)

Example 1 is repeated with the varnish formula given in Example 1, but with a polyester prepared from a dicarboxylic acid mixture consisting of terephthalic acid and isophthalic acid in a molar ratio of 3:7 and a dialcohol mixture consisting of TCD-diol and 2,2-dimethylpropanediol-1,3 in a molar ratio of 1:3, plus a small amount of ethyleneglycol as impurity, and a relative viscosity of 1.64 (corresponding to German Offenlegungsschrift No. 2,934,443).

EXAMPLE 6

20.0 weight-parts of a polyester of terephthalic acid and TCD-diol, prepared as in Example 1, but having a relative viscosity of 1.41, are dissolved in 50.7 weight-parts of a mixture of SOLVESSO 150 ® and SOLVESSO 200 ® in a weight ratio of 4:1, and pigmented with 25.8 weight-parts of titanium dioxide, and ground to a paste. Then 3.4 weight-parts of a commercial blocked polyisocyanate resin (IPDI Adduct B 1370 delivered as a 60% solution in butyl acetate and phenol, mfr. Veba-HÜLS) and 0.1 weight-parts of dibutyl tin dilaurate are added. The coating is baked for 12 minutes at 160° C. to form a layer approximately 10 μm thick.

TABLE

| Example No. | | | 1 | 2 | 3 | 4 | 5 | 6 | A | B | C |
|---|---|---|---|---|---|---|---|---|---|---|---|
| Stability during Sterilization | | | | | | | | | | | |
| a. | Water, neutral | | 0 | 0 | 0 | 0 | 0 | 0 | 0 | 0 | 0 |
| b. | Lactic acid, | 1 wt.-% sol. | 0–1 | 0–1 | 0–1 | 1 | 0–1 | 0–1 | 3 | 3 | 3 |
| c. | Same, | 2 wt.-% sol. | 1 | 1 | 1 | 1–2 | 1 | 1–2 | 6 | 6 | 6 |
| d. | Same, | 3 wt.-% sol. | 2 | 2 | 2 | 2–3 | 2 | 2–3 | 10 | 10 | 10 |
| e. | Citric/ tartaric acid | 0.5/ 1 wt.-% sol. | 0–1 | 0–1 | 0–1 | 1 | 0–1 | 0–1 | 3 | 3 | 3 |
| f. | Sodium chloride/ acetic acid | 3/ 2 wt.-% sol. | 0 | 0 | 0 | 0 | 0 | 0 | 1 | 1 | 1 |
| Pliability | | | | | | | | | | | |
| Impact formability (mm) | | | 40 | 35 | 40 | 50 | 60 | 35 | 68 | 53 | 45 |
| Erichsen cup test (mm) | | | 1.0 | 1.0 | 0.7 | 0.5 | 0.5 | 0.5 | 0.5 | 0.5 | 0.5 |

Test media b to f: The diluent was water

It will be understood that the specification and examples are illustrative but not limitative of the present invention and that other embodiments within the spirit and scope of the invention will suggest themselves to those skilled in the art.

What is claimed is:

1. Thermosetting coating compositions comprising at least one binding agent and a solvent wherein the binding agent consists of
   (a) 5 to 35 weight-parts of a triazine resin or a capped polyisocyanate resin and
   (b) 95 to 65 weight-parts of at least one of saturated, linear polyester of dicarboxylic acids and disols, the polyester having a relative viscosity between 1.3 and 1.8, and where a dicarboxylic acid content comprises moieties of terephthalic and/or isophthalic acid and the diol content consisting of 100 to 70 mole-% of bis-(hydroxmethyl)-tricyclodecane and 0 to 30 mole-% of at least one other diol.

2. Thermosetting coating composition as claimed in claim 1 also containing varnish additives selected from pigments, fillers and varnish adjuvants.

3. Thermosetting coating composition as claimed in claim 1, wherein said triazine resin (a) is a benzoguanamine resin.

4. Thermosetting coating composition as claimed in claim 1, wherein said component (a) is a capped polyisocyanate resin.

5. Thermosetting coating composition as claimed in claim 1, wherein said dicarboxylic acid of component (b) comprises moieties of at least one of terephthalic and isophthalic acid and in addition comprises up to 10 mole-% of moieties of other dicarboxylic acids.

6. Thermosetting coating composition as claimed in claim 1, wherein said other diol of component (b) consists essentially of 2,2-dimethylpropanediol-1,3.

7. Thermosetting coating composition as claimed in claim 1, wherein the dicarboxylic acid moieties are primarily terephthalic acid moieties.

8. Thermosetting coating composition as claimed in claim 1, wherein the dicarboxylic acid moieties are primarily isophthalic acid moieties.

9. Thermosetting coating composition as claimed in claim 1, wherein said dicarboxylic acids are 50 mole-% terephthalic acid and 50 mole-% isophthalic acid.

10. Method of varnishing a metal substrate comprising applying to the metal substrate a thermosetting coating composition as claimed in claim 1.

* * * * *

UNITED STATES PATENT AND TRADEMARK OFFICE
CERTIFICATE OF CORRECTION

PATENT NO. : 4,452,954

DATED : June 5, 1984

INVENTOR(S) : Gerhard Schade et al.

It is certified that error appears in the above-identified patent and that said Letters Patent is hereby corrected as shown below:

Claim 1, line 7, "disols" should be -- diols --.

Signed and Sealed this

Sixteenth Day of April 1985

[SEAL]

Attest:

DONALD J. QUIGG

Attesting Officer     Acting Commissioner of Patents and Trademarks